United States Patent [19]

Schmid-Schönbein

[11] 4,135,819
[45] Jan. 23, 1979

[54] APPARATUS FOR MEASURING THE AGGREGATION RATE OF PARTICLES

[75] Inventor: Holger Schmid-Schönbein, Aachen-Laurensberg, Germany

[73] Assignee: Ernst Leitz GmbH, Marl, Germany

[21] Appl. No.: 758,707

[22] Filed: Jan. 12, 1977

Related U.S. Application Data

[63] Continuation of Ser. No. 559,259, Mar. 17, 1975, abandoned.

[30] Foreign Application Priority Data

Mar. 20, 1974 [DE] Fed. Rep. of Germany ....... 2413285

[51] Int. Cl.² .......................................... G01N 33/16
[52] U.S. Cl. .................................. 356/39; 23/230 B
[58] Field of Search ................................. 356/39-42, 356/197, 208, 209; 73/64.1; 128/26; 23/230 B

[56] References Cited

U.S. PATENT DOCUMENTS

3,307,392  3/1967  Owen et al. ........................ 356/40

OTHER PUBLICATIONS

Zivlstra; W.G. "Syllektometrie," from "Oxymetrie, Theorie und Klinische Anwendung," Georg Theme Publisher, Stuttgart, 1960, pp. 117-119, Eng. Trans.
Schmid-Schönbein et al., "A Counter-Rotating Rheoscope Chamber" for the Study of the "Microrheology of Blood Cell aggregation by Microscopic Observation & Microphotometry," Microvascular Research 6, 1973, pp. 366-376.

*Primary Examiner*—John K. Corbin
*Assistant Examiner*—Wm. H. Punter
*Attorney, Agent, or Firm*—Gilbert L. Wells

[57] ABSTRACT

Apparatus for measuring the aggregation rate of particles in liquids, comprising a transparent mixing chamber, a drive causing mixing, a photoelectric system for observing the mixed material in the chamber, and an analysis system following the photoelectric system, where the output signals are fed to a display and/or a warning and/or a memory system. The apparatus is applied to quickly ascertain information disclosing blood subsidence from a minimum amount of blood (capillary native blood free of coagulation inhibitor).

10 Claims, 5 Drawing Figures

APPARATUS FOR MEASURING THE AGGREGATION RATE OF PARTICLES

This is a continuation, of application Ser. No. 559,259, filed Mar. 17, 1975, now abandoned.

CROSS REFERENCES TO RELATED APPLICATIONS

Applicant claims priority under 35 U.S.C. 119 for Application P 24 13 285.2, filed Mar. 20, 1974 in the Patent Office of the Federal Republic of Germany.

BACKGROUND OF THE INVENTION

The present application relates to apparatus for measuring the rate at which particles suspended in a transparent solution comglomerate and to a special purpose application of this apparatus.

As is known, human red corpuscles when in the presence of certain eggwhite bodies of blood plasma combine into large aggregates. These aggregates are the so-called money rolls (international terminology: "rouleaux"). This is the cause of the suspension lability, i.e., the sedimentation of the red blood corpuscles in the standing blood made viscous. One of the routine examinations most frequently used in medicine rests on the determination of the sedimentation rate, i.e., the determination of the settling rate of the blood corpuscles in cylindrical glass tubes. The methods used were disclosed by Westergren or by Wintrobe. Whenever the composition of the plasma eggwhite bodies is interfered with in a characteristic manner, there is an increased aggregation, (that is) large aggregates are formed, which will settle faster in accordance with known laws of physics (Stoke's law of sedimentation).

It is further known that in the presence of sufficient forces, for instance in the flow condition, these aggregates are again dispersed, to reform again at once upon termination of the forces. The process of aggregate formation therefore is arbitrarily reversible.

Conventional measurement of the blood aggregation potential is obtained from blood subsidence, 4 ml of blood being taken from the patient's arm vein and mixed with 1 ml of coagulation-inhibiting solution. Then this diluted blood is drawn up to a height of 200 mm in special tubes. The tubes are placed in the vertical position. Because of the downward sedimentation of the erythrocytes, which is influenced by the upward flow of the blood plasma, there is a reference level of red blood corpuscles with respect to the cell-free plasma. The number of mm by which this level drops after 1 and after 2 hours is read off and allows conclusions regarding illnesses.

This process requires a relatively large amount of blood, and furthermore is time consuming and is subject to spurious effects because of many different factors, and there have been many attempts to record the scope and the aggregation rate of red blood corpuscles in other ways. Thus the text "Oxymetrie, Theorie und Klinische Answendung" (Theory and Clinical Application of Oxymetry) by George Thieme publishers, Stuttgart, at pp 117–119, reveals the method of first rapidly stirring blood in a photometer and then measuring the decrease in reflection of the blood when there is no flow, this decrease being caused by the conglomeration of red blood corpuscles. However, the theoretical basis of these methods is uncertain.

Attempts furthermore have been undertaken to measure the influence of the aggregates on the apparent blood viscosity for slow flow by means of highly sensitive rotational viscosimeters.

Lastly, several attempts have been disclosed to accelerate the sedimentation rate by using either sedimentation tubes at an angle or else by subjecting the tubes to stronger forces in centrifuges.

All of the methods cited suffer from the drawback that they record only the consequences of the aggregation but not the aggregation process itself. These consequences vary extremely depending on the different measurement techniques used, and fundamentally may not be circumvented. Essentially this is so because the magnitude of the aggregates do not remain constant during sedimentaion and these aggregates are affected by the plasma flowing past them. Furthermore, the number of red blood corpuscles varies from patient to patient and hence affects the size of the aggregates as well as the space available to them in a complex manner. Unraveling effects between the thick suspension of aggregates and the thin blood plasma appreciably interferes with the measuring process of viscosimetry.

SUMMARY OF THE INVENTION

Having in mind the limitations of the prior art, it is an object of the present invention to provide an apparatus for directly recording the aggregation process and which is as free as possible from the above cited artifact interferences. A further object is to provide a time of measurement as short as possible.

The apparatus of the present invention for measuring the aggregation rate of particles in a liquid, comprises a transparent mixing chamber, a drive for performing the mixing, a photoelectric system to observe the mixture in the chamber, and an analysis system following the photoelectric system, the analysis output signals being fed to a display and/or warning and/or memory system. The apparatus of the present invention is used to obtain rapidly the information corresponding to native blood free of coagulation inhibitor subsidence from a minimum amount of blood (capillary blood). A body penetrating the mixing chamber may be used as the drive providing mixing, this body being powered by a motor with a quick shut-off device. The body may be designed as a rotational one. The mixing chamber and the rotary body may be so dimensioned with respect to each other that significant centrifugal forces do not occur in the blood being tested for given speeds of rotation. The mixing chamber may also be in the shape of a tube. The mixing chamber may be movably supported, and a drive may be provided to that end. The mixing chamber may consist at least in part of a flexible material and the mixing will then take place by deforming the elastic chamber parts. Lastly, optical components may be inserted in the beam path between the light source and the photoelectric detectors, which will affect the phase and/or the amplitude of the light.

As shown by tests performed, the new and unexpected results of the present invention consist in achieving appreciable reductions in time because, contrary to the above described prior art blood subsidence method, the test results are available within one minute and the physician is therefore capable of immediately treating the patient. When the present invention is carried out, a significantly smaller amount of blood is required for examination, and this is an important factor with ailing infants or small children, or with the injured. Nor is it necessary to withdraw this blood from an arm vein, rather it is enough to withdraw it from a finger or from the ear lobe. Because of the rapidity of the test, there is no need to add a coagulation inhibitor, and the blood corpuscles undergo no changes in this short time as might cause spurious results. Lastly, such small amounts of blood are used for testing that they are free from sedimentation effects as occur in larger quantities and which also introduce spurious effects.

BRIEF DESCRIPTION OF THE PREFERRED EMBODIMENTS

The present invention may best be explained by reference to the appended drawings, wherein.

DESCRIPTION OF THE PREFERRED EMBODIMENTS

Figures 1, 1A, 1B:
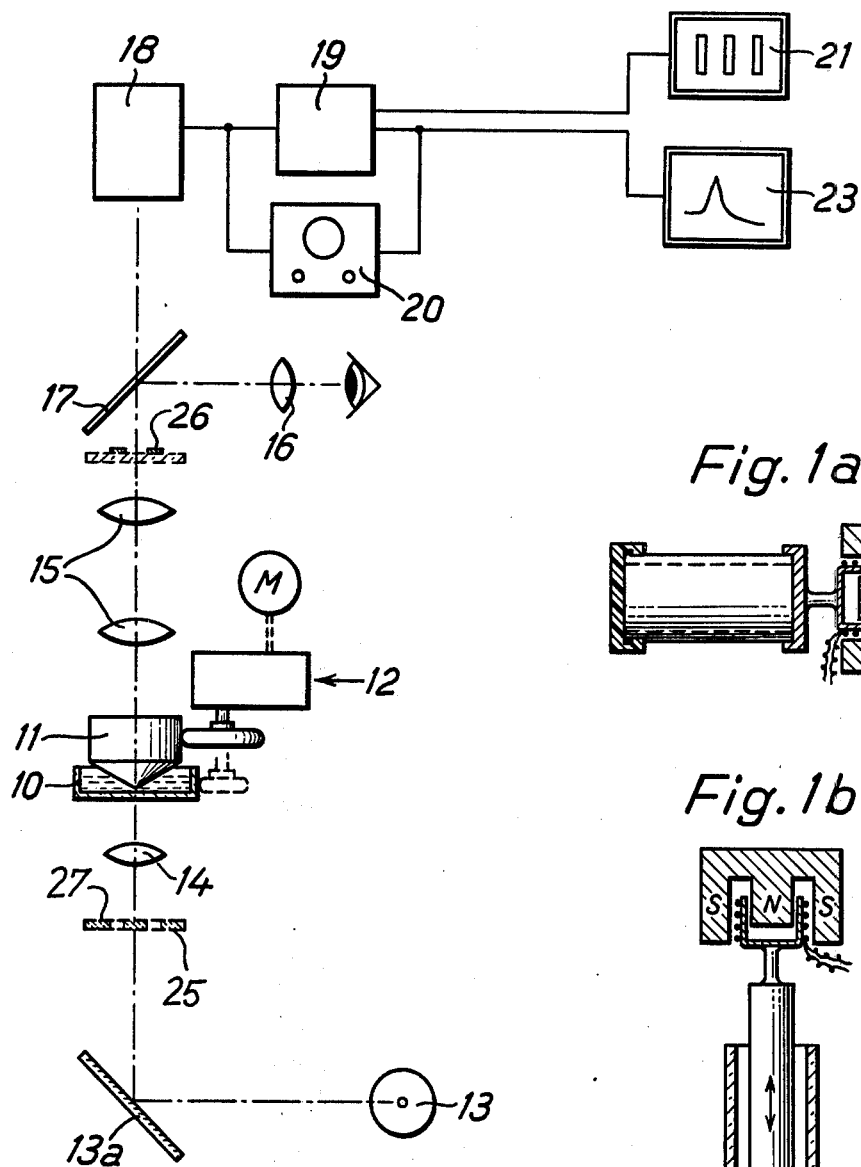
FIG. 1 is a plan view of an embodiment of the apparatus of the present invention shown in diagrammatic form.
FIGS. 1a and 1b show other embodiments for mixing tub.
Figure 2:
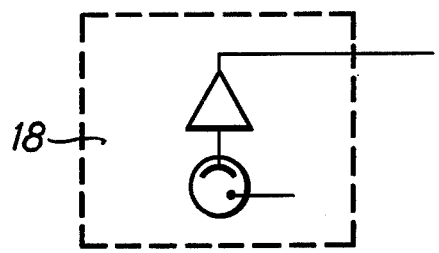
FIG. 2 is a detailed showing of an embodiment for the photoelectric system 18 of FIG. 1.
Figure 3:
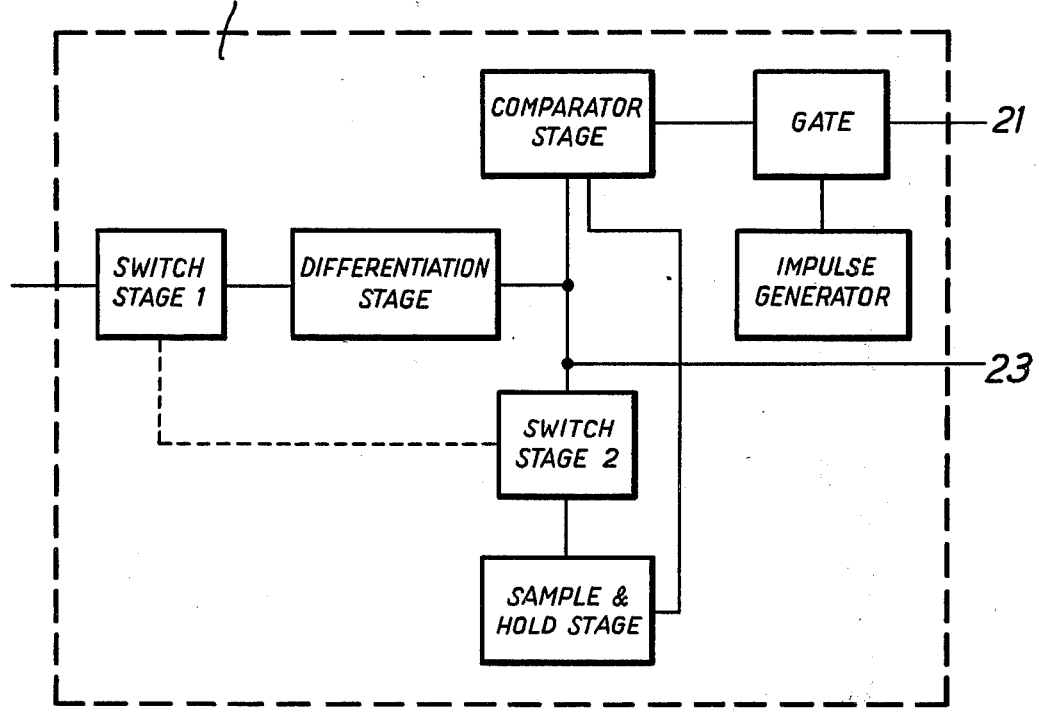
FIG. 3 is a detailed showing of an embodiment for the analyzing stage 19 of FIG. 1.

As shown in FIG. 1, the apparatus of the present invention comprises a mixing chamber in the design of a tub 10 receiving the blood to be tested. A cone 11 pivotable about its axis of rotation causing the mixing process penetrates this tub. The tub and cone are made of a transparent material and so dimensioned that for a given range of rotational speeds of the cone, no significant centrifugal forces will be applied to the blood being tested. A drive 12 equipped with fast shut-off actuates cone 11 which thus disperses the blood particles. Tub and cone are illuminated from a light source 13 by means of a deflecting mirror 13a and a condenser 14. Visual observation of the test substance is made possible by an objective 15 and a splitter 17 and an ocular 16. Splitter 17 is followed by a photoelectric system 18 which shapes as shown in FIG. 2 the light flux that comes from the tub, cone, objective and splitter into proportional electric signals. An analyzing stage 19 follows this system 18, ascertaining the modification of the output signals from equipment 18 and providing the first derivative of the output signals as a function of time.

In addition to the above description, optical components (reference numerals 25, 26) are inserted along the optical axis of FIG. 1. These components on account of their special design affect the light amplitude alone of both the light amplitude and phase. As shown, the components in the given embodiment consist of a stop 25 with circular aperture 27 positioned in front of chamber 10, and of an annular structure located in a conjugate plane and adapted in its dimensions to the image of annular stop 25. When this structure for instance is a dyed-in layer, then both the amplitude and the phase of the light reaching detector 18 will be affected. When structure 26 is a neutral density filter, only the light amplitude will be affected. The two measures are appropriate when the object to be examined predominantly affects the phase, but not the amplitude of the light.

As determined by means of special methodology (see Microvascular Research, 1973, pp. 366-376), the exponential decay of this derivative runs parallel to (the curve of) erthrocyteaggregate formation. It may be observed for instance visually on the oscilloscope 20 of FIG. 1 in parallel with stage 19. If therefore the blood being tested is put into motion by rotating the cone, existing particle aggregates dissolve. But they will reform if cone rotation is stopped and hence the blood returns to rest. This causes the mentioned change in transparency and hence a change in the output signals from equipment 18. One may determine the half value period, which for human blood lies between 0.4 and 10 seconds, by using simple electronic means at stage 19. This half value period then allows computing its reciprocal value in terms of the time constant of the initially mentioned particle aggregates. Half value period or time constants may be displayed digitally at stage 21 following stage 19, or they may be stored in a memory 23. These components 21 and 23 are disclosed in U.S. Pat. Nos. 3,317,736, FIG. 3 and 3,306,095, FIG. 1. When using a warning system, the instrumentation shown may also be used for series (assembly line) tests.

Thus one records the change in optical density of the blood by means of a display photoelectric system, this change occurring by the conversion of a homogeneous, well-mixed fast flowing suspension of erythrocytes into a static one of aggregate linked erythrocyte lumps, the optical transmittance (of the latter) increasing in accordance with known physical laws. The increase in amplitude of the photoelectric signals and their first derivatives are recorded as function of time.

The above offers but one of many possible embodiments. Thus, tub and rotational body might also be made spherical. Again, the mixing chamber itself may be used to disperse the substance by being supported elastically and being shaken for instance by one or several piezo electric resonators or oscillators, or by a loud speaker. In such cases the chamber appropriately will be of tubular form (FIG. 1a). Again, one may disperse the blood inside a tubular mixing chamber by the to-and-fro motion of a stirrer dipping into the tube and the motion of which may be stopped abruptly (FIG. 1b).

In special applications it may be advantageous to display and/or measure the phase changes caused by the particles. Suitable optical components, for instance, light rings, phase rings, beam splitters and beam combining elements as disclosed in U.S. Pat. Nos. 2,601,175, FIG. 2 and 2,553,108, FIG. 1 may be inserted into the illumination and projection paths.

Furthermore, measurement may be undertaken in the reflection rather than transmission mode. Obviously the apparatus must be designed accordingly.

I claim:

1. Apparatus for rapidly ascertaining the information disclosing blood subsidence from a minimum amount of native blood by measuring the natural aggregation rate of particles in liquid blood, comprising:
   (a) means for illuminating and defining an optical axis;
   (b) upper (11) and lower (10) means defining a transparent anti-aggregation chamber therebetween for being filled with a minimum amount of blood specimen, said blood specimen touching said upper and lower means and located along said optical axis;
   (c) drive means for agitating said anti-aggregation chamber by way of slow motion of said upper means relative to said lower means and for separating said blood specimen;
   (d) rapid shut-off means to stop said agitated chamber;

(e) photoelectric receiver means responsive to illumination leaving said anti-aggregation chamber;

(f) means for deriving electrical signals from said photoelectric receiver means after stopping said chamber over the whole aggregation time; and (g) an analyzing stage for providing the first derivative of said electrical signals as a function of time, said derivative being indicative of the blood subsidence of said blood specimen.

2. The apparatus of claim 1, wherein said upper means comprises a body (11) penetrating said lower means comprising mixing chamber (10) and said drive means is actuated by a motor drive (12) contacting said upper means and equipped with a rapid shut-off.

3. The apparatus of claim 2, wherein said body penetrating into mixing chamber (10) is a rotating body (11).

4. The apparatus of claim 3, wherein said mixing chamber (10) and said rotating body (11) are so dimensioned in their respective shapes that for given rotational speeds of the rotating body, there is no significant centrifugal force applied to the blood being tested.

5. The apparatus of claim 1, wherein said upper means is movably supported and in that said drive means contacts and rotates said upper means.

6. The apparatus of claim 1, wherein optical components influencing the phase and the amplitude of the illumination are inserted in said optical axis between said means for illumination and said photoelectric receiver means.

7. The apparatus of claim 1, wherein optical components influencing the amplitude of the illumination are inserted in said optical axis between said means for illumination and said photoelectric receiver means.

8. In a method for obtaining measured values from blood sedimentation, by inserting a blood specimen in a transparent measuring chamber, erythrocytes aggregation present in the specimen is removed, the specimen is illuminated with light and the amount of light leaving the specimen over a given time is measured, the improvement comprising:

(a) said specimen is native blood inserted in a measuring chamber having upper (11) and lower (10) means movable relative to one another and the specimen comes in contact with said upper and lower means;

(b) erythrocytes aggregation present in said specimen is counteracted by movement of said upper means relative to said lower means;

(c) the amount of light leaving said specimen during the aggregation process setting in again is photometrically measured after sudden stopping of the movement of said upper and lower means and a photometric signal is generated; and (d) the first derivative of said photometric signal as a function of time is determined.

9. The method of claim 8, wherein the half value time of the derived function is ascertained and indicated.

10. The method of claim 8, wherein the reciprocal value of the half value is formed as a formation constant of the erythrocytes aggregate and indicated.

* * * * *